US008879808B2

(12) United States Patent
Vaillant

(10) Patent No.: US 8,879,808 B2
(45) Date of Patent: Nov. 4, 2014

(54) SYNCHRONIZATION OF MEDICAL IMAGING SYSTEMS

(75) Inventor: Régis Vaillant, Villebon sur Yvette (FR)

(73) Assignee: General Electric Company, Schenectady, NY (US)

(*) Notice: Subject to any disclaimer, the term of this patent is extended or adjusted under 35 U.S.C. 154(b) by 67 days.

(21) Appl. No.: 13/327,798

(22) Filed: Dec. 16, 2011

(65) Prior Publication Data

US 2012/0170825 A1 Jul. 5, 2012

(30) Foreign Application Priority Data

Dec. 17, 2010 (FR) ..................................... 10 60726

(51) Int. Cl.
A61B 6/00 (2006.01)
A61B 5/0456 (2006.01)

(52) U.S. Cl.
CPC . A61B 6/00 (2013.01); A61B 6/463 (2013.01); A61B 5/0456 (2013.01)
USPC .......................................................... 382/128

(58) Field of Classification Search
None
See application file for complete search history.

(56) References Cited

U.S. PATENT DOCUMENTS 5,771,895 A * 6/1998 Slager ........................... 600/462
6,491,629 B1 * 12/2002 Bousseljot et al. ........... 600/300
6,546,274 B2 * 4/2003 Itagaki et al. ................. 600/413
6,643,392 B1 * 11/2003 Vaillant et al. ................ 382/132
7,211,045 B2 * 5/2007 Dala-Krishna et al. ....... 600/441
7,529,393 B2 5/2009 Peszynski et al.
7,853,307 B2 * 12/2010 Edwards ....................... 600/424
8,233,688 B2 * 7/2012 Soubelet et al. .............. 382/131
8,303,505 B2 * 11/2012 Webler et al. ................. 600/447

(Continued)

FOREIGN PATENT DOCUMENTS

WO 20040034329 A2 4/2004
WO 2006035398 A1 4/2006
WO WO 2006035398 A1 * 4/2006

OTHER PUBLICATIONS

Abboud et al. "The use of cross-correlation function for the alignment of ECG waveforms and rejection of extrasystole" 1984.*

(Continued)

Primary Examiner — Amir Alavi
Assistant Examiner — Alexander J Lesnick
(74) Attorney, Agent, or Firm — Global Patent Operation; Marc A. Vivenzio

(57) ABSTRACT

A method for interventional imaging of synchronizing a first dataset with a second dataset is provided. The datasets represent a region of interest in a patient, wherein the first dataset and the second dataset each corresponding to two different types of information on the region of interest and wherein the datasets are acquired by separate medical systems. The method comprises aligning the first dataset and the second dataset with at least two signals representing a physiological activity of the patient, the at least two signals having been recorded by the medical systems on a common time scale with the time scale used for acquiring the datasets.

17 Claims, 4 Drawing Sheets

(56) References Cited

U.S. PATENT DOCUMENTS

| | | |
|---|---|---|
| 2004/0077952 A1 | 4/2004 | Rafter et al. |
| 2005/0288578 A1* | 12/2005 | Durlak ................. 600/434 |
| 2006/0079759 A1* | 4/2006 | Vaillant et al. ........... 600/424 |
| 2007/0016029 A1* | 1/2007 | Donaldson et al. ........ 600/437 |
| 2007/0027390 A1* | 2/2007 | Maschke et al. .......... 600/425 |
| 2008/0152205 A1* | 6/2008 | Vaillant et al. ........... 382/132 |
| 2008/0154122 A1* | 6/2008 | Vaillant et al. ........... 600/424 |
| 2008/0287803 A1* | 11/2008 | Li et al. ................. 600/466 |
| 2008/0306766 A1 | 12/2008 | Ozeki et al. |
| 2009/0208079 A1* | 8/2009 | Vaillant et al. ........... 382/131 |
| 2010/0030068 A1 | 2/2010 | Vaillant et al. |
| 2010/0099979 A1 | 4/2010 | Schoonenberg et al. |
| 2011/0019878 A1* | 1/2011 | Soubelet et al. ............ 382/107 |

OTHER PUBLICATIONS

Leung et al. "Digitization of Electrocardiogram (ECG) signals using delta-sigma modulation" 1998.*
Cioffi "Chapter 6: Fundamentals of Synchronization" 2006.*
Morales et al. "Digitization and Synchronization Method for Electrocardiogram Printouts" 2005.*
French Search Report dated Jul. 20, 2011 which was issued in connection with French Application No. 1060726 which was filed on Dec. 17, 2010.

* cited by examiner

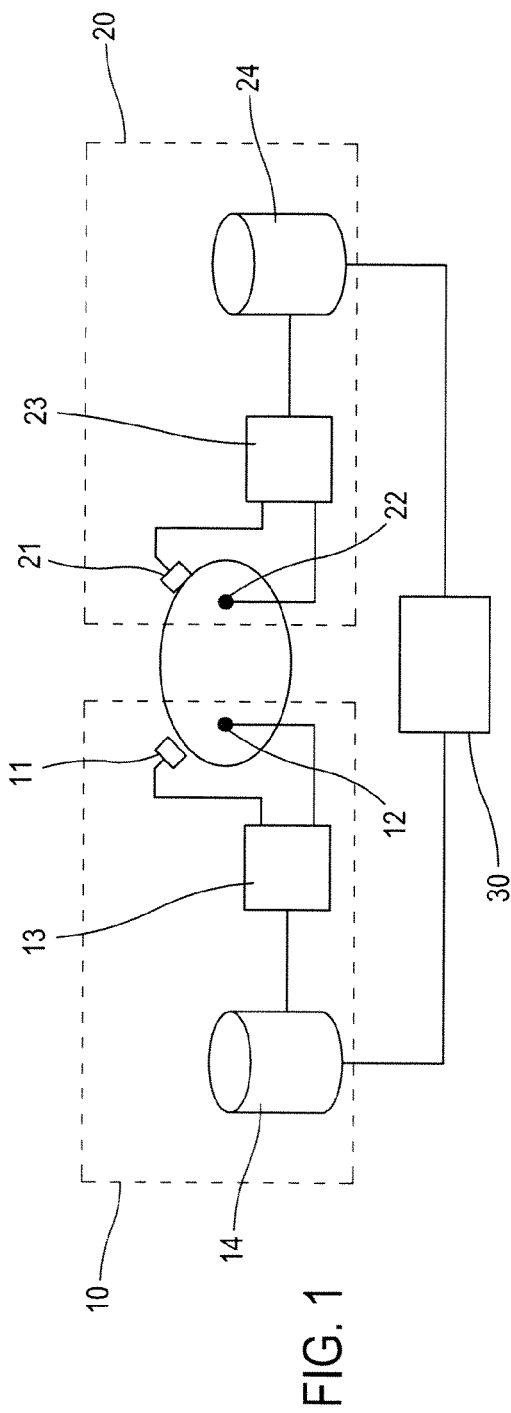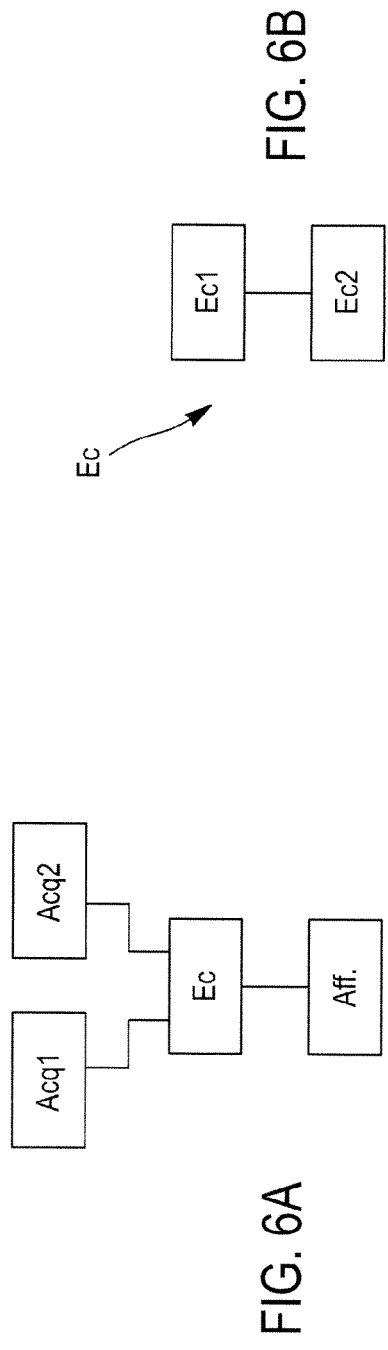

SYNCHRONIZATION OF MEDICAL IMAGING SYSTEMS

BACKGROUND OF THE INVENTION

1. Field of the Invention

The present disclosure relates to the field of medical imaging. It more particularly concerns the processing of data, notably, images used by a practitioner during procedure on a patient.

2. Description of the Prior Art

For the diagnosis and treatment of coronary diseases, the form of the vessels is analyzed. For this purpose, a practitioner guides and deploys a surgical instrument inside the vascular system of a patient while being assisted by a medical imaging system. Said medical imaging system allows the acquisition, processing and real-time visualization of two-dimensional images (2D) representing the patient's vascular system and the surgical instrument. With these images, the practitioner is able to guide the instrument inside the vascular system.

For diagnosis, defects such as stenosis (abnormal narrowing of a blood vessel) must be detected. To do so, the practitioner may either be provided with a radiological image of a region of interest in a patient, into which a contrast product has been injected, or with a radiological image delivered by an intravascular sensor or other data derived from said sensor.

It is advantageous to be provided with such data at the same time, so that the practitioner is able to have a view or detailed information on the inner side of a vessel, but also an overall view to aid in guiding the sensor.

The problem then arises of synchronizing the two types of data items: those delivered by the medical imaging system and those delivered by the intravascular sensor. These different data items effectively derive from two separate imaging systems having different acquisition rates.

BRIEF SUMMARY OF THE INVENTION

Embodiments of the present invention allow for the synchronizing of medical data delivered by separate imaging systems According to an embodiment of the present invention, a method for interventional imaging of synchronizing a first dataset with a second dataset is provided. The datasets represent a region of interest in a patient, wherein the first dataset and the second dataset each corresponding to two different types of information on the region of interest and wherein the datasets are acquired by separate medical systems. The method comprises aligning the first dataset and the second dataset with at least two signals representing a physiological activity of the patient, the at least two signals having been recorded by the medical systems on a common time scale with the time scale used for acquiring the datasets.

According to another embodiment of the present invention, a processing unit connected to at least two medical imaging systems is provided. The processing unit is configured to: synchronize a first dataset with a second dataset, wherein the datasets represent a region of interest in a patient, the first dataset and the second dataset each corresponding to two different types of information on the region of interest, and wherein the datasets are acquired by separate systems of the at least two medical imaging systems; and align the first dataset and the second dataset with at least two signals representing a physiological activity of the patient, the at least two signals having been recorded by the medical systems on a common time scale with the time scale used for acquiring the datasets.

BRIEF DESCRIPTION OF THE DRAWINGS

The accompanying drawings, which are incorporated in and constitute a part of the specification, illustrate one or more embodiments and, together with the description, explain these embodiments. In the drawings:

FIG. 1 illustrates two medical imaging systems to acquire images of a region of interest in a patient in accordance with an embodiment of the present invention;

FIGS. 6a and 6b illustrate steps of a method in accordance with an embodiment of the present invention.

DETAILED DESCRIPTION OF THE INVENTION

Figure 3:
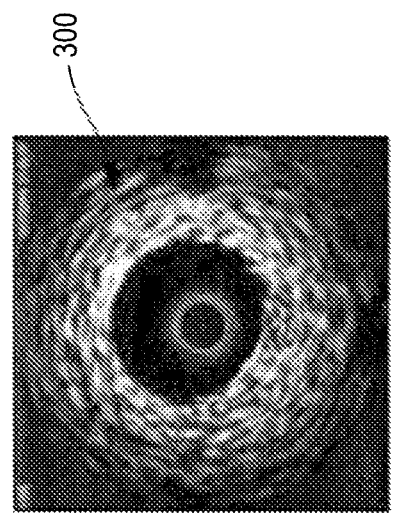
FIG. 3 illustrates an image delivered by an intravascular imaging sensor in accordance with an embodiment of the present invention.

FIG. 1 illustrates two separate medical systems 10, 20. In one embodiment, the first and second systems 10, 20 are medical imaging systems. In this case, the first medical imaging system 10, for example, allows for the acquisition of radiological images of a region of interest in a patient (not illustrated) in which a contrast product has been injected.

In one embodiment, said imaging system 10 comprises an X-ray source and a detector arranged facing the source, the source and detector being connected via a C-arm. The detector may be a semiconductor image sensor, for example, comprising caesium iodide phosphorus on a transistor/photodiode array in amorphous silicon. Other suitable detectors are: CCD sensor, direct digital detector converting X-rays directly into digital signals.

The second medical imaging 20 comprises an intravascular probe 21, for example, intended to be inserted into an artery of the region of interest. This probe comprises a sensor used to acquire images, or simply local properties, of a vessel such as temperature for example. In this respect, different types of probes exist. Typically, the practitioner guides this probe 21 into the region of interest of the patient.

The systems 10, 20 each comprise a device 12, 22 to acquire a signal representing a physiological activity of the patient. The physiological activity of the patient may be, for example, the patient's heart beats or respiratory movement.

Advantageously, the devices to acquire the signal representing the patient's physiological activity allow acquisition of the same type of signal. On the other hand, the devices to acquire the signal representing the patient's physiological activity are not similarly regulated: they have different acquisition rates.

In one embodiment, the medical systems respectively comprise a control unit 13, 23 and a storage unit 14, 24. For the first medical imaging system 10, the control unit 13 is used, for example, to control the position of the C-arm and various parameters for image acquisition. For the second medical system 20, the control unit 23 is used, for example, to control various parameters for the acquisition of images or data.

The control unit 13, 23 may comprise a reader device (not illustrated) for example a diskette reader, a CD-ROM, DVD-ROM reader, or connection ports to read the instructions for the processing method from an instruction medium (not illustrated) e.g. a diskette, CD-ROM, DVD-ROM, or USB flash drive or more generally any removable memory medium, or via a network connection.

The storage units 14, 24 allow the storage of acquired images/data and storage of the signal representing the patient's physiological activity delivered by each system 10, 20.

Each medical system 10, 20 may further comprise a display unit (not illustrated). One single display unit may be provided for the two imaging systems. A display unit is for example a computer screen, a monitor, flat screen, plasma screen or any other known type of display device.

To achieve aligning of the images delivered by the two medical systems, the data derived from each system 10, 20 and the signals representing the physiological activity of the patient are transmitted to a processing unit 30. Said processing unit 30 is for example at least one processor, at least one microcontroller, at least one programmable logic controller, at least one application-specific integrated circuit, other programmable circuits, or other devices which include a computer such as a work station.

As a variant, the processing unit 30 may comprise a reader device (not illustrated) e.g. a diskette reader, CD-ROM or DVD-ROM reader, or connection ports to read the instructions for the processing method from an instruction medium (not illustrated) e.g. a diskette, CD-ROM, DVD-ROM or USB flash drive or in general any removable memory medium or via a network connection.

The transfer from each storage unit 14, 24 towards the processing unit 30 can take place via a computer network, via a wire or via wireless connection.

Figure 2:
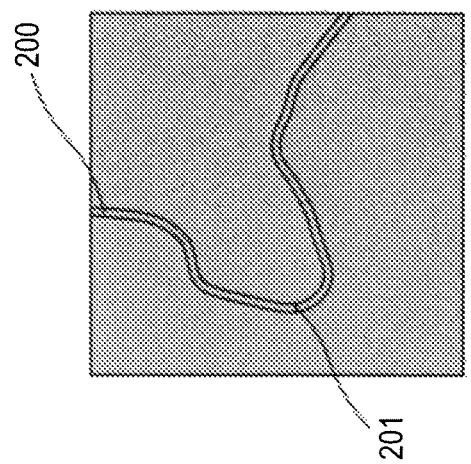
FIG. 2 illustrates a radiological image of a region of interest in a patient in accordance with an embodiment of the present invention.

FIG. 2 illustrates an image of a region of interest in a patient, in which a contrast product has been injected. In this image, a vessel 200 can be seen in which an image sensor 201 has been inserted. The first dataset consists of a succession of images of this type: images of the region of interest in the patient.

FIG. 3 illustrates an image of the inside of the vessel 200 acquired by an image sensor 201 at the position such as illustrated in FIG. 2. The second dataset here consists of a succession of images of this type. In general, the image sensor 201 is able to acquire data which are not images. The purpose here is to cause the images derived from the first medical imaging system to coincide with the data derived from the sensor 201.

The data derived from the medical systems is respectively acquired, $Acq_1$, $Acq_2$, at the first and second acquisition rates or first and second time scales during respective acquisition periods. Here the acquired data Acq1, Acq2 may be of variable type, and can just as well be mono-dimensional signals, or two-dimensional (2D) or three-dimensional (3D) data. The acquisition periods are not necessarily identical. Each medical system also records one or more physiological signal(s), and each of the systems is independently capable of positioning the recordings of the physiological signal(s) and acquired data on its own time scale.

Therefore, for each medical system, the data is acquired at the same rate or on a common time scale with the recording of the physiological signal. The recording intervals of the physiological signals attached to the two datasets must overlap so that synchronization of the two datasets is possible. For a given medical system, it is possible to align an image/data item with an instant of a signal representing the physiological activity of the patient.

The processing unit 30 allows the synchronizing of datasets derived from different medical systems. For this purpose, during an aligning step $E_c$, the signals representing the physiological activity of the patient are caused to coincide.

Figure 4:
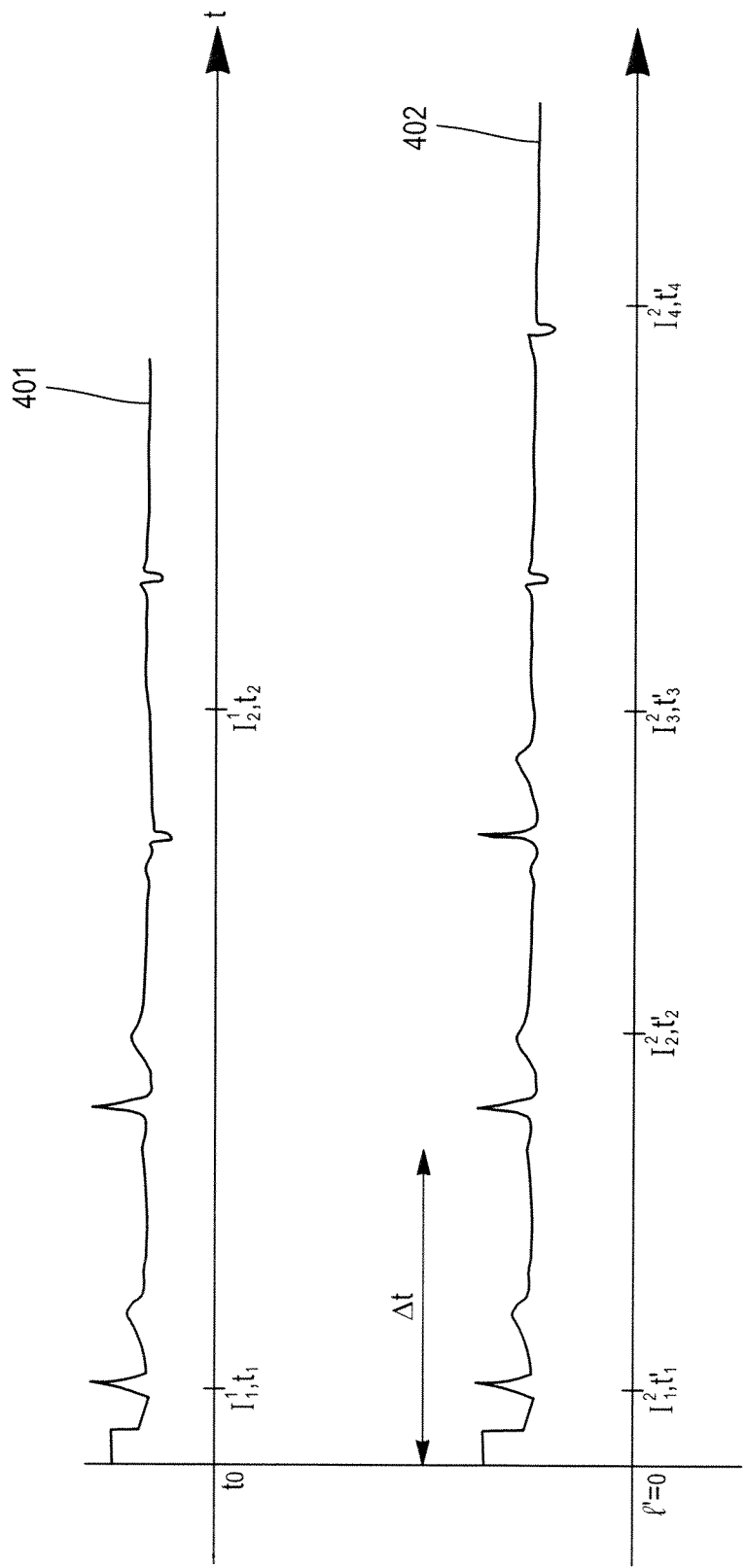
FIG. 4 illustrates the synchronizing of images on a synchronization signal conforming to in accordance with an embodiment of the present invention.

FIG. 4 illustrates two signals representing the patient's physiological activity. The signal 401 (top) is the signal acquired by the first medical system and the signal 402 (bottom) is the signal acquired by the second medical system. In this figure, these represent images acquired by two medical imaging systems, the data being images.

In addition the acquisition times of the images are indicated: at time $t_1$ the image $I_1^1$ of the first assembly is acquired; at time $t_2$ the image $I_2^1$ of the first assembly is acquired; at time $t'_1$ the image $I_1^2$ of the second assembly is acquired; at time $t'_2$ the image $I_2^2$ of the second assembly is acquired; at time $t'_3$ the image $I_3^2$ of the second assembly is acquired; and at time $t'_4$ the image $I_4^2$ of the second assembly is acquired.

Depending on the medical systems used, acquisitions take place over a few seconds and may reach more than thirty seconds in some cases.

It is ascertained that the signals representing the patient's physiological activity, although derived from the same source, do not have the same origin. The acquisitions did not start at the same time: t=0 for one and t'=0 for the other. There therefore exists a time shift Δt between the two, which must be determined to obtain one same origin for the different acquisition times.

Therefore, the aligning step consists of synchronizing the signals representing the patient's physiological activity delivered by each medical system. To synchronize these signals, it is possible to proceed by correlation to determine any time shift Δt between the two signals.

Once synchronized, since each data item can be positioned on a common time scale with the signal describing the physiological activity of the patient, it is possible to align the data items. The synchronization of the patient's physiological activity allows one single time reference to be obtained for all data.

For image data, said alignment of the images with one another allows a position of the intravascular image sensor to be related with an image of the vessel at this position. As already mentioned, it is possible to relate a data item such as temperature with a precise position of an intravascular sensor. The practitioner is therefore provided with two data items simultaneously, since the data items that have been aligned are displayed simultaneously.

Figure 5:
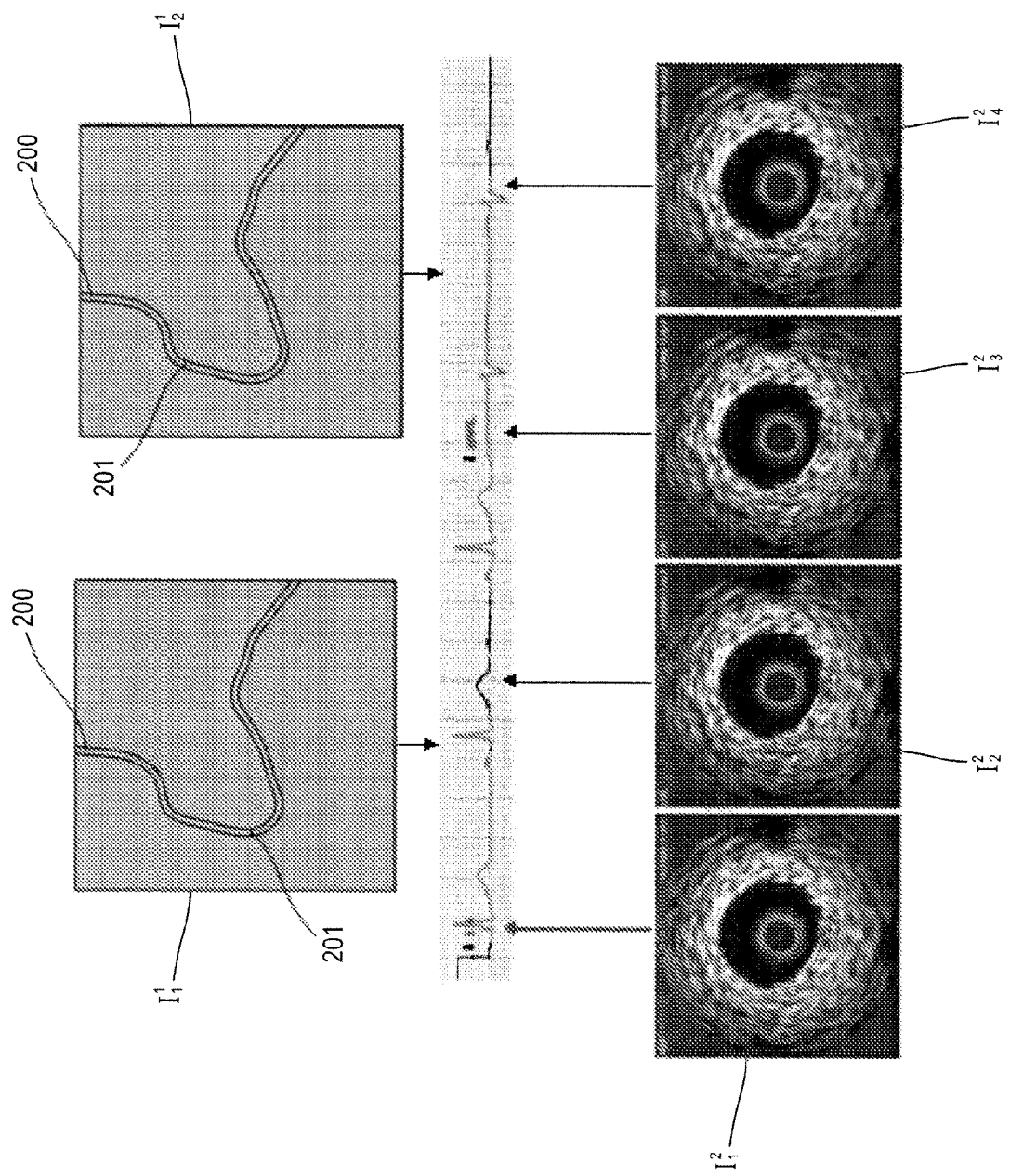
FIG. 5 illustrates images aligned with each other using a method according to in accordance with an embodiment of the present invention.

FIG. 5 illustrates images derived from two datasets aligned with a signal representing the patient's physiological activity (here the signal acquired by the second medical imaging system). For display, Aff, provision may be made to display the images of the region of interest on a first line, the signal representing the patient's physiological activity on a second line, and the images of the inner side of the vessel on a third line.

In this manner, the synchronization signal corresponding to the signals representing the patient's physiological activity acts as a time reference for all the images. For the aligning of data, it is possible to modulate the signal representing the patient's physiological activity with an aperiodic signal derived from an external source. The same aperiodic signal is used for each acquisition of the physiological signal. The aperiodic nature facilitates correlation between signals to determine any time shift between the signals delivered by the different imaging systems.

The above-described method can be applied to a higher number of medical systems, and in this case multiple synchronizations are possible.

The method described in the foregoing can advantageously be implemented in the form of a computer programme comprising machine instructions for conducting the above-described method.

What is claimed is:

1. A method for interventional imaging of synchronizing a first dataset with a second dataset, wherein the datasets represent a region of interest in a patient, the first dataset and the second dataset each corresponding to two different types of information on the region of interest, and wherein the datasets are acquired by separate medical systems, the method comprising:
generating a synchronized signal from a first signal and a second signal; and
aligning the first dataset and the second dataset with the synchronized signal,
wherein the first signal and the second signal represent a physiological activity of the patient as measured by respectively, a first device and a second device, one each found on the separate medical systems,
wherein the first signal has an acquisition rate that is different from the acquisition rate of the second signal,
wherein the first signal and the second signal are recorded by the first device and the second device of the medical systems on a common time scale with the time scale used for acquiring the datasets,
wherein the first signal and the second signal are synchronized to the synchronized signal by,
determining a time shift between the first signal and the second signal that reflects the different acquisition rates of the first signal and the second signal, and
from the time shift, setting the origin of the first signal and the second signal on the common time scale, and
wherein the origin of the synchronized signal acts as a time reference for the first dataset and the second dataset on the common time scale, and the synchronized signal is partly or fully modulated with an external aperiodic signal generated by a source external to one or the other of the medical systems.

2. The method according to claim 1, wherein the first dataset and the second dataset comprise a succession of images in which the region of interest of the patient can be visualized.

3. The method according to claim 1, further comprising correlating the synchronized signal to each dataset, wherein the time shift between the first signal and the second signal corresponds to maximum correlation.

4. The method according to claim 1, wherein one dataset is offset from the other dataset, and wherein aligning the first dataset and the second dataset further comprises applying the determined time shift to the acquisition times of the first dataset offset from the second dataset.

5. The method according to claim 1, wherein the physiological activity of the patient comprises the patient's heart or patient's respiratory movement.

6. The method according to claim 1, wherein the first dataset is derived from acquisitions by an intravascular image sensor, the second dataset is derived from acquisitions by an X-ray medical imaging system, and the data comprises images.

7. The method according to claim 1, further comprising displaying the data of the first dataset and the second dataset aligned with each other and with the synchronized signal simultaneously.

8. The method according to claim 1, further comprising:
acquiring, on a first common time scale, the first dataset and the signal representing the patient's physiological activity acquired by the first medical system; and
acquiring, on a second common time scale, the second dataset and the signal representing the patient's physiological activity acquired by the second medical system.

9. A processing unit connected to at least two medical systems, the processing unit configured to:
generate a synchronized signal from a first signal and a second signal; and
align a first dataset and a second dataset with the synchronized signal, the first dataset and the second dataset representing a region of interest in a patient, the first dataset and the second dataset each corresponding to two different types of information on the region of interest,
wherein the first dataset and the second dataset are acquired by separate medical systems of the at least two medical systems;
wherein the first signal and the second signal represent a physiological activity of the patient as measured by respectively, a first device and a second device, one each found on the separate medical systems,
wherein the first signal has an acquisition rate that is different from the acquisition rate of the second signal,
wherein the first signal and the second signal are recorded by the first device and the second device of the separate medical systems on a common time scale with the time scale used for acquiring the datasets,
wherein the first signal and the second signal are synchronized to the synchronized signal by,
determining a time shift between the first signal and the second signal that reflects the different acquisition rates of the first signal and the second signal,
from the time shift, setting the origin of the first signal and the second signal on the common time scale, and
wherein the origin of the synchronized signal acts as a time reference for the first dataset and the second dataset on the common time scale, and the synchronized signal is partly or fully modulated with an external aperiodic signal generated by a source external to one or the other of the separate medical systems.

10. The processing unit according to claim 9, wherein the first dataset and the second dataset comprise a succession of images in which the region of interest of the patient can be visualized.

11. The processing unit according to claim 9, wherein the processing unit is further configured to correlate the synchronized signal to each dataset, wherein the time shift between the first signal and the second signal corresponds to maximum correlation.

12. The processing unit according to claim 9, wherein the first dataset is offset from the second dataset, and wherein the processing unit is further comprised to apply the determined time shift to the acquisition times of the first dataset offset from the second dataset.

13. The processing unit according to claim 9, wherein the physiological activity of the patient comprises the patient's heart or patient's respiratory movement.

14. The processing unit according to claim 9, wherein the first dataset is derived from acquisitions by an intravascular image sensor, and wherein the second dataset is derived from acquisitions by an X-ray medical imaging system, the data being images.

15. The method according to claim 9, further comprising displaying the data of the datasets aligned with each other and with the synchronized signal simultaneously.

16. The processing unit according to claim 9, further comprising:
acquiring, on a first common time scale, the first dataset and the signal representing the patient's physiological activity acquired by one of the separate medical systems; and
acquiring, on a second common time scale, the second dataset and the signal representing the patient's physiological activity acquired by the other of the separate medical systems.

17. A system, comprising:
a first medical system configured to acquire a first signal having a first origin;
a second medical system configured to acquire a second signal having a second origin that is different from the first origin; and
a processing unit coupled to each of the first medical system and the second medical system, the processing unit configured with a processor, memory, and executable instructions for processing the first signal and the second signal,
wherein the first signal and the second signal are acquired at different acquisition rates, and
wherein the executable instructions comprise instructions for,
generating a synchronized signal from the first signal and the second signal having a third origin at which the first origin of the first signal is coincident with the second origin of the second signal, wherein the synchronized signal is partly or fully modulated with an external aperiodic signal generated by a source external to one or the other of the first and second medical systems, and
displaying an image from the first medical system and an image from the second medical system simultaneously with the synchronized signal.

* * * * *

UNITED STATES PATENT AND TRADEMARK OFFICE
CERTIFICATE OF CORRECTION

PATENT NO. : 8,879,808 B2  
APPLICATION NO. : 13/327798  
DATED : November 4, 2014  
INVENTOR(S) : Vaillant Page 1 of 1

It is certified that error appears in the above-identified patent and that said Letters Patent is hereby corrected as shown below:

In the Claims

In Column 7, Line 4, in Claim 15, delete "method" and insert -- processing unit --, therefor.

Signed and Sealed this
Twenty-first Day of April, 2015

Michelle K. Lee
*Director of the United States Patent and Trademark Office*